(12) United States Patent
Horak (10) Patent No.: US 7,837,942 B2
(45) Date of Patent: Nov. 23, 2010

(54) ALLERGY TEST CHAMBER

(76) Inventor: Friedrich Horak, Panoramastrasse 156, Innermanzing (AT) A-3052

( * ) Notice: Subject to any disclaimer, the term of this patent is extended or adjusted under 35 U.S.C. 154(b) by 1518 days.

(21) Appl. No.: 10/343,469

(22) PCT Filed: Nov. 22, 2001

(86) PCT No.: PCT/AT01/00370

§ 371 (c)(1),
(2), (4) Date: Jan. 30, 2003

(87) PCT Pub. No.: WO02/41784

PCT Pub. Date: May 30, 2002

(65) Prior Publication Data

US 2004/0054262 A1    Mar. 18, 2004

(30) Foreign Application Priority Data

Nov. 23, 2000   (AT) .............................. A 1974/2000

(51) Int. Cl.
*B01L 3/00* (2006.01)
*B01L 1/04* (2006.01)
(52) U.S. Cl. .......................................... 422/99; 454/187
(58) Field of Classification Search ................... 422/99; 454/187

See application file for complete search history.

(56) References Cited

U.S. PATENT DOCUMENTS 3,701,235 A * 10/1972 Isaacson ....................... 95/196

(Continued)

FOREIGN PATENT DOCUMENTS

WO          99/16315          4/1999

(Continued)

OTHER PUBLICATIONS

Day, James H., Briscoe, Maureen P., Environmental exposure unit: a system to test anti-allergic treatment, Aug. 1999, Annals of Allergy, Asthma, & Immunology, vol. 83, Issue 2, pp. 83-89.*

(Continued)

*Primary Examiner*—Lore Jarrett
(74) *Attorney, Agent, or Firm*—Drinker Biddle & Reath LLP (57) ABSTRACT

The invention relates to an allergy test chamber comprising at least one inlet for supplying allergen-free air, especially fresh air, into the chamber. Said chamber is characterised in that the at least one inlet (23) for allergen-free air is provided with an air flow distribution device (26, 27), and in that the allergy test chamber (20) also comprises at least one inlet (25) for allergen test particles, such as plant pollen or mite faeces, and at least one outlet (24) for removing air loaded with allergen test particles from the chamber by means of suction. Said outlet (24) is arranged at a distance from the inlets (23, 25) for allergen-free air and allergen test particles. Said air movement principle i.e. introducing air into the chamber, mixing it with a defined quantity of allergens, and removing by suction the allergen-loaded air to another area of the chamber, enables uniformity of the distribution of the allergen particles in the test chamber to be significantly improved, compared with known allergy test chambers wherein allergen-loaded air is circulated in the test chamber.

22 Claims, 6 Drawing Sheets

U.S. PATENT DOCUMENTS

| | | | | | |
|---|---|---|---|---|---|
| 3,976,450 | A | * | 8/1976 | Marcote et al. | 96/12 |
| 4,059,903 | A | * | 11/1977 | Piet et al. | 312/1 |
| 5,331,991 | A | * | 7/1994 | Nilsson | 135/93 |
| 5,533,501 | A | * | 7/1996 | Denyer | 128/203.12 |
| 5,830,058 | A | * | 11/1998 | Røsjø | 454/187 |
| 5,865,171 | A | * | 2/1999 | Cinquin | 128/203.12 |
| 5,935,516 | A | * | 8/1999 | Baugh | 422/1 |

FOREIGN PATENT DOCUMENTS

| | | | |
|---|---|---|---|
| WO | WO0032150 | * | 6/2000 |

OTHER PUBLICATIONS

Ronborg, et al: "Exposure chamber for allergen challenge. The development and validation of a new concept" *Allergy* (Denmark), vol. 51, No. 2 pp. 82-88 (Feb. 1996).

Horak, et al: "Efficacy and tolerability of astemizole-D and Loratadine-D during prolonged, controlled allergen challenge in the Vienna Challenge Chamber" *Arzneimittel-Forschung* (Germany), vol. 46, No. 11, pp. 1077-1081 (Nov. 1996).

Htut, et al: "A pilot study on the effect of one room mechanical ventilation with heat recovery (MVHR) units on house dust mite populations and Der p1 levels in laboratory simulated bedrooms and on ambient conditions in an occupied bedroom in Cambridge, UK" *International Journal of Environmental Health Research*, vol. 6, No. 4, pp. 301-313 (1996).

* cited by examiner

FIG. 8b

ALLERGY TEST CHAMBER

BACKGROUND OF THE INVENTION

The present invention relates to an allergy test chamber having at least one inlet for supplying allergen-free air, especially fresh air, into the chamber.

Figure 1:
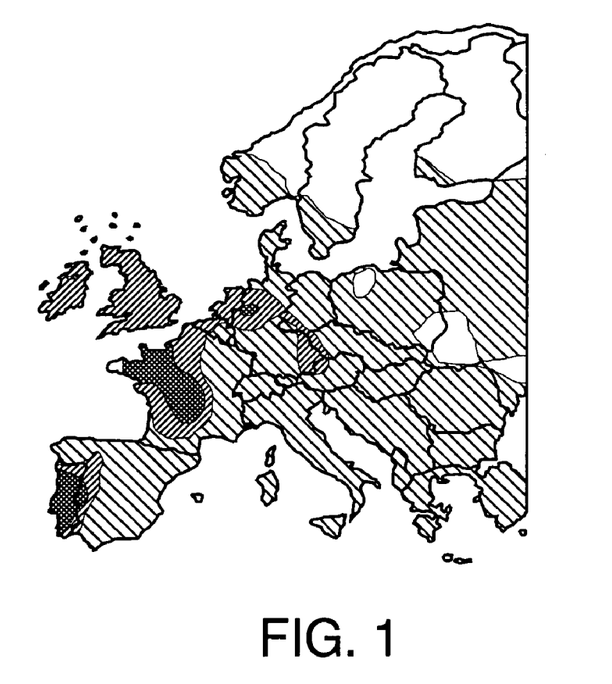
FIG. 1 shows the concentration of grass pollen in Europe on Jun. 10, 2000, darker areas indicating higher concentrations.
Figure 2:
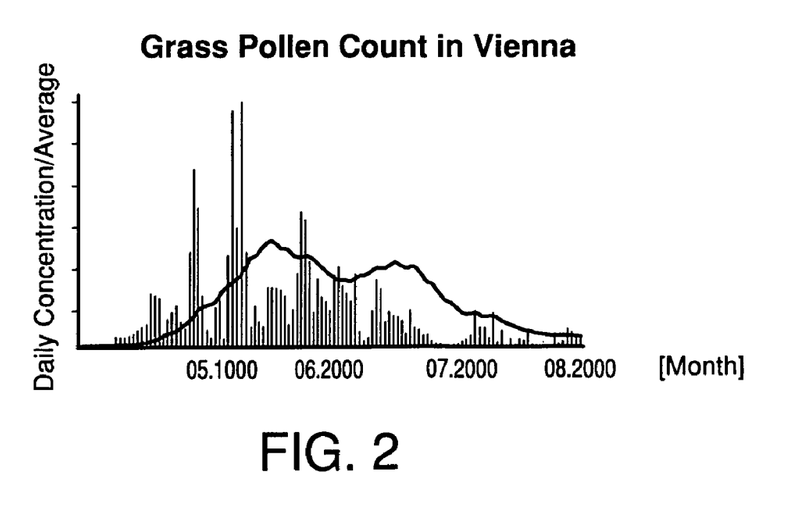
FIG. 2 shows the seasonal variation and the average grass pollen count of 20 years.

The effectiveness of anti-allergy treatment can only be evaluated objectively if allergic subjects are monitored under the natural load of a specific allergen, as for instance grass pollen. The potential use of data which have been obtained within the framework of such a clinical study carried out under environmental conditions is severely restricted by the extreme fluctuation of allergen concentration in the air. Not only does it vary from one region to the other, as shown in FIG. 1 by way of the concentration of grass pollen in Europe on Jun. 10, 2000, the dark areas indicating high concentration levels and the light areas representing low pollen concentration, from one year to the next and within one season (see FIG. 2, showing seasonal variations and the average grass pollen count of 20 years), but also within one day and quite substantially with the distance from ground level. In addition, patients' reactions to allergens in the air vary considerably in the course of one season because of a priming effect and other less important phenomena. These problems are brought to light more clearly with subjectively tolerable symptoms, like conjunctivitis, less clearly with rhinitis and rarely ever with severe attacks, like asthma.

Another problem is the consistent registration over a period of several days, as it can almost only be achieved by a subjective evaluation of symptoms. The reliability of documentation in diaries kept by patients declines with every day of the study. In order to obtain statistical material that can be used in studies for doses finding, effectiveness or duration of effect, a large number of patients and long periods of observation are necessary. However, a low amount of pollen and many other environmental factors may lead to unexpectedly insignificant results in field studies.

Therefore it is necessary to find a solution for clinical experiments with patients suffering from allergies to pollen and house-dust mites which come close to field studies without having their disadvantages.

At present tests carried out in allergy test chambers are undisputedly known as "Golden Standard" by means of which the above problems can be overcome (Cartier A., et al., "Guidelines for bronchoprovocation on the investigation of occupational asthma", Report of the Subcommittee on Provocation for Occupational Asthma. J Allergy Clin Immunol 1989, 84:823-829); Melillo G., "European Academy of Allergy and Clinical Immunology—Provocation tests with allergens", Allergy 1997, Suppl. 35, 52:1-35). These chambers make it possible to carry out tests by inhaling allergens under controlled conditions coming close to natural load and furthermore guaranteeing precise and comprehensive results for every patient. As an allergen test chamber enables exact studies while generating a large number of numerical data, they make it possible for the researcher to obtain statistically significant results with a by far lower number of patients than would be required in a field study.

The so far most sophisticated allergy test chamber comprises a room sealable with respect to external air wherein a number of fans are disposed, which circulate the air horizontally within the room. Allergens, e.g. grass pollen or mite faeces, are introduced into the air within the room by putting up one or several cups containing a predetermined amount of allergens in front of respective fans and swirling them by the draft caused by the fan. It is attempted to remedy the relatively unequal distribution of allergens within the room thus achieved by instructing the test subjects to change their positions within the room at regular time intervals.

It would be desirable to have an allergy test chamber guaranteeing a considerably improved uniformity of allergen load of the air within the room thus further improving objectivization and reproducibility of test with test subjects.

BRIEF SUMMARY OF THE INVENTION

This aim is achieved according to the invention by developing the above allergy test chamber in such a way that at least one inlet for allergen-free air is provided with an air flow distribution device and that the allergy test chamber furthermore comprises at least one inlet for allergen test particles, such as plant pollen or mite faeces, and at least one outlet for removing air loaded with allergen test-particles from inside the chamber by means of suction, the outlet being arranged at a distance from the inlets for allergen-free air and allergen test particles. Surprisingly it has turned out that turning away from the known principle of circulating allergen-laden air within the test chamber, as described above, in favor of a ventilation principle, where the air is introduced into the chamber, mixed with a defined quantity of allergens, and the allergen-laden air is again sucked off at a different position of the chamber, brings about a considerably improved uniformity of the distribution of allergen particles within the test chamber, as shown below in more detail by means of a graph.

An embodiment of the invention easy to construct is characterized in that the at least one inlet for allergen-free air comprises an air supply pipe having a plurality of through-openings in the pipe wall.

In order to achieve superior uniformity of distribution and, as the case may be, swirling or the generation of turbulent air flow within the allergy test chamber, it might be provided for the air flow distribution device to be equipped with air nozzles, preferably spherical nozzles, oriented in different directions. Alternatively thereto the air flow distribution device may comprise baffle plates or air distribution combs.

Preferably the inlets for supplying allergen test particles and allergen-free air are spaced apart, but in a different embodiment they may also be integrated one within the other, in case suitable air flow paths around the inlets for supplying the test particles are provided for.

In a preferred embodiment of the allergy test chamber according to the invention the inlets for supplying allergen test particles and allergen-free air are arranged in the ceiling of the chamber and/or in at least one side-wall of the chamber close to the ceiling, and the at least one outlet for sucking off air loaded with allergen test particles is arranged in the floor of the chamber and/or in at least one side-wall of the chamber close to the floor.

In order to ensure optimum air quality within the chamber at least one multi-layer filter system aimed at reducing pollutants is advantageously inserted in the flow path of allergen-free air into the chamber.

Allergen test particles tend to aggregate in case of increased air humidity. In order to prevent such aggregations from influencing the clinical tests, a device for de-agglomerating the allergen particles to be introduced into the chamber is advantageously provided.

In order to reach the additional objective of semi- or fully automatic operation of the allergen test chamber, according to the invention a device for automatically metering allergen test particles and their continuous or intermittent supply into the chamber is preferably provided, pressure or partial vacuum systems preferably serving to convey the particles. The device for automatic metering may comprise screw micro-conveyors, tooth-wheel micro-conveyors, Archimedean screw micro-conveyors, rotary micro-sieve disks, centrifugal selection, electromagnetic or electrostatic dosing fields. Semiautomatic operation may be realized using micro dosing-spoons.

In order to ensure highly uniform introduction of the allergen test particles into the allergen test chamber, a particle distributor may be connected to the at least one inlet for allergen test particles, the particle distributor preferably being arrangeable in such a way that the allergen test particles are introduced at those points where the allergen-laden air has a flow interference of zero. A preferred embodiment of a particle distributor comprises a body having an axial bore and radial bores extending from the axial bore to the outer periphery of the distributor. Alternatively the particle distributor may comprise a body having oriented comb-like exit openings. Furthermore the particle distributor advantageously has a baffle plate close to the inlet for allergen test particles, the allergen test particles being conveyed through the inlet by means of compressed air.

In order to create preset and reproducible air conditions for the clinical tests, according to one embodiment of the invention a climate module for controlling climate parameters like temperature, humidity, air throughput, etc. of the allergen-free air supplied into the interior of the chamber is provided, the climate module preferably being equipped with a real-time control circuit for controlling the parameters.

In order to prevent allergen test particles from escaping through openings in the allergy test chamber, as for instance doors or service hatches, the barometer pressure within the chamber is reduced as compared to the barometer pressure outside the chamber. The pressure differential preferably is 10-200 Pa.

The allergy test chamber according to the invention preferably has at least one measurement instrument for identifying representative parameters of the introduced allergen test particles. Here, measurement instruments for measuring the particle concentration of the air within the chamber may be provided. In order to measure the individual allergen load at least one measurement instrument each should be provided for every test subject in the chamber. Preferably at least one particle collection device for accumulating the absolute particle quantity introduced in the course of one time unit is furthermore provided for the purpose of subsequently analyzing essential allergen parameters.

BRIEF DESCRIPTION OF THE DRAWINGS

The invention will now be explained in more detail by way of a non-limiting embodiment. In the drawings.

DETAILED DESCRIPTION OF THE DRAWINGS

Chamber Design

Figure 3:
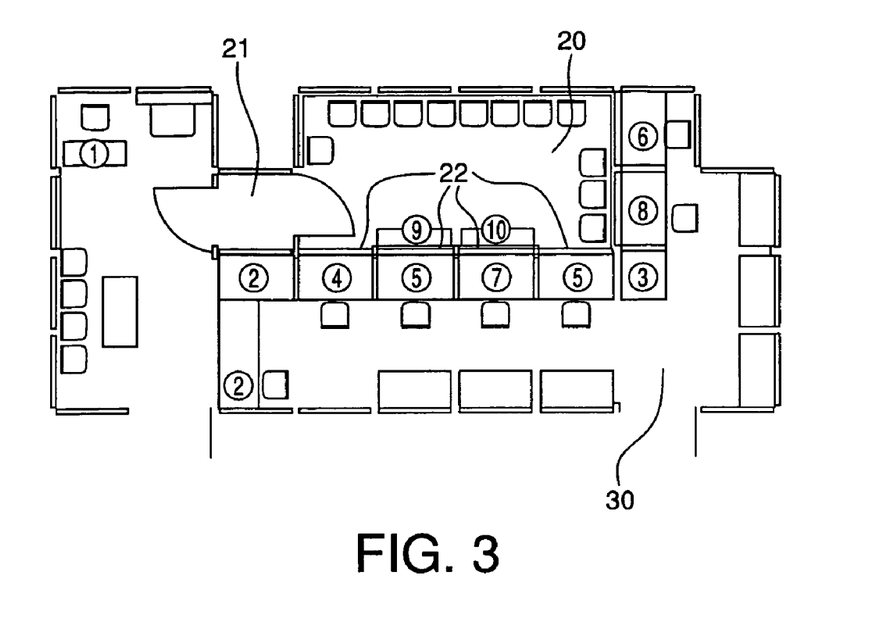
FIG. 3 shows a ground plan of the test chamber and the working space surrounding it.
Figure 4:
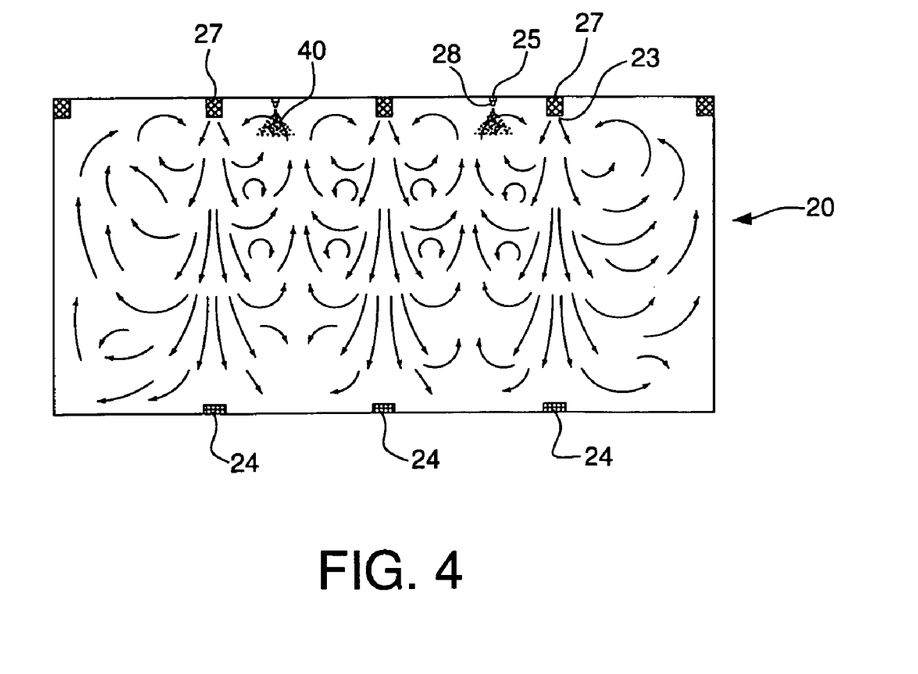
FIG. 4 is a vertical plan of the test chamber.

The allergen test chamber 20 according to the invention (in the following sometimes abbreviated as VCC for "Vienna Challenge Chamber") is a closed system filled with room air. With its length of 5.25 meters and a width of 2.60 meters the VCC comprises an area of 13.65 square meters, and at an average height of 2.70 m, it has a volume of about 37.20 cubic meters. FIG. 3 shows the ground plan of the allergen test chamber 20 together with the working space 30 associated therewith, and FIG. 4 is a vertical plan thereof. The VCC 20 is entered through an air lock 21 of 1.30 square meters having pollen stripping mats and a "settling device" on the floor, respectively. The chamber seats up to 14 patients that may be tested simultaneously for several hours (usually 2 to 8 h, depending on the aim of the test) under controlled and reproducible conditions. Four windows 22 between chamber 20 and the surrounding working space 30 allow the constant observation and examination or questioning of the patients tested. Numbers (1) to (10) indicate examination and test positions, respectively, of which positions (1) to (8) are within working space 30, while positions (9) and (10) are within the test chamber 20. Smooth aluminum surfaces, antistatic measures and regular thorough cleaning between test sessions reduce allergen adhesion which could lead to irregular allergen concentrations.

Ventilation

Figure 7:
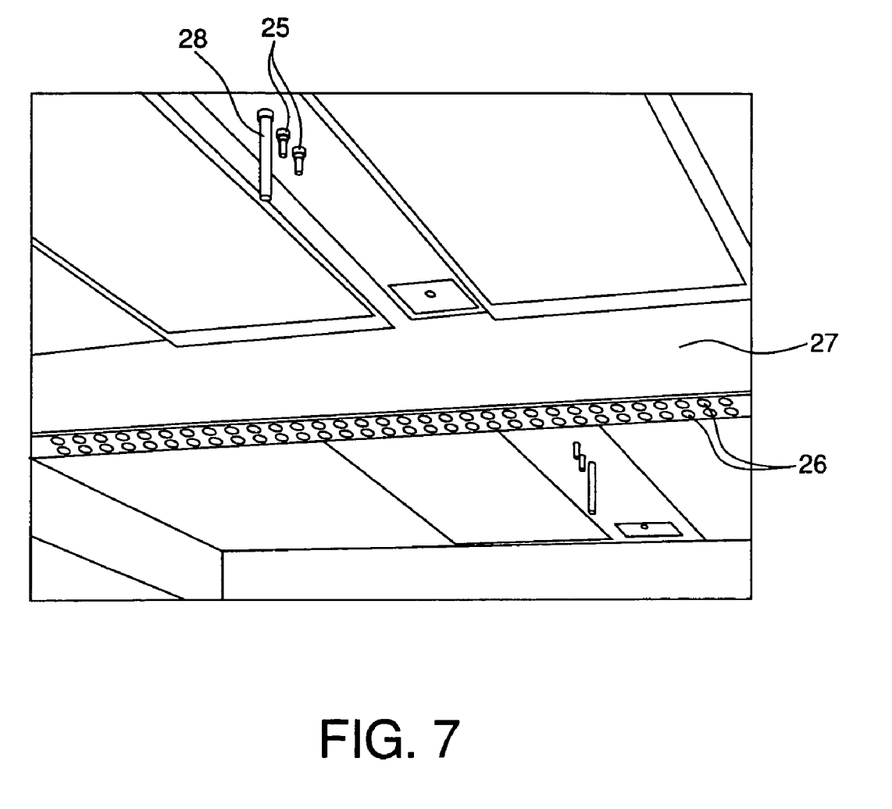
FIG. 7 is a perspective view of an inventive ventilation strip with spherical nozzles.

An automatic air supply system into the chamber guarantees permanent and uniform air conditioning. The temperature, usually in a range of 24 to 26 degrees Centigrade, is recorded online (every 5 seconds) at four different locations of the chamber 20 at a height of 2.2 meters, just like the relative humidity, which is usually kept within a range of 4 to 45%. A stable temperature is reached about 15 minutes after the test session is started, there only being a variation of 0.5° C. and 1.5% humidity. Furthermore, the $CO_2$ concentration is recorded online (every 5 seconds) at a single point 0.5 meters above ground level. The $CO_2$ concentration is kept within the range of 0.1% throughout the test session regardless of the number of patients tested and the duration of the test. Allergen-free air is blown into the chamber 20 through 384 inlets 23 in the ceiling, causing a constant and slightly turbulent air flow as shown in FIG. 4. The 384 inlets 23 shown schematically in FIG. 2 are formed by spherical nozzles 26 (see FIG. 7) mounted on the wall of an air supply pipe 27. The spherical nozzles are oriented in different directions, thus providing for the turbulent flow. The turbulent air flow in turn leads to a homogeneous distribution of allergen test particles within the chamber. Used air is sucked off through six outlets 24 close to the floor. The amount of fresh air supplied is calibrated with respect to the number of patients in the test chamber. In order to guarantee that no air from the test chamber will contaminate the working space or other parts of the building, the pressure inside the chamber is kept about 60 Pa below that outside.

Allergen Distribution in the Chamber

Figure 5:
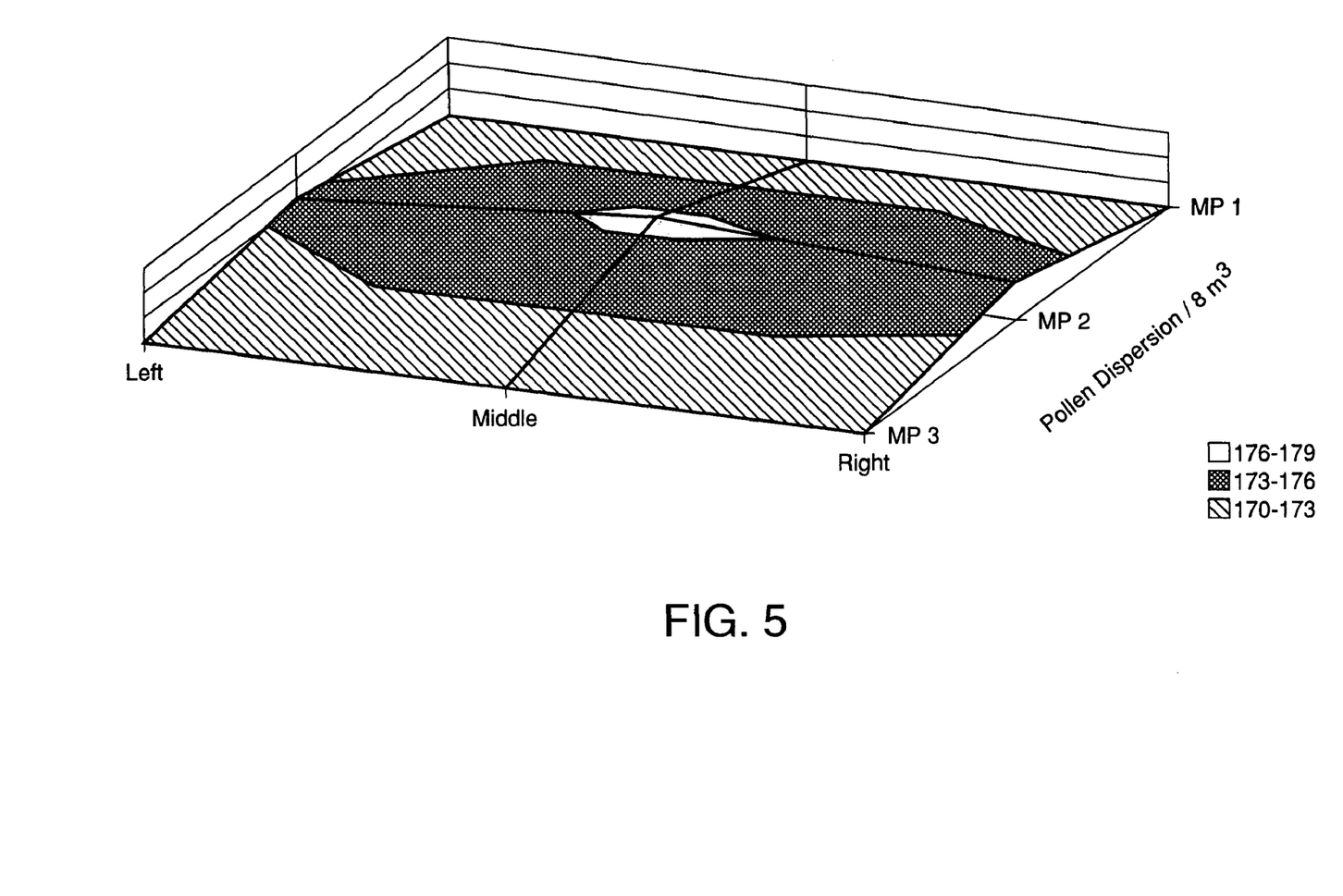
FIG. 5 shows the distribution of pollen load at a height of 1.5 m in the test chamber according to the invention.
Figure 6:
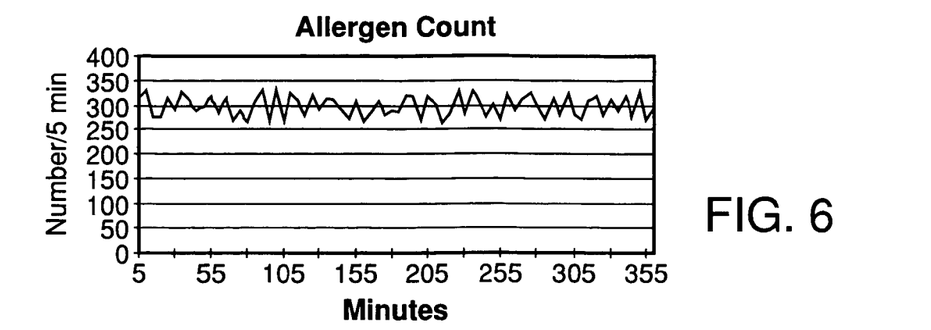
FIG. 6 shows the variation of pollen load in the course of a 6 h test session in the test chamber.

In order to introduce allergen test particles into the chamber 20, separate circuits are provided wherein predetermined quantities of allergen particles 40 are blown into the chamber 20 through inlets 25 by means of compressed air. For each separate allergen (e.g. grass pollen, birch pollen, house-dust mite faeces, etc.) a separate supply system is installed in order to prevent the contamination by different allergens. Genuine house-dust mite faeces or pollen grains are automatically supplied into the chamber 20 from the outer working space 30. First the allergens are sucked into the circuit by vacuum, then the respective allergen is dispensed into the chamber under pressure. The discharge of the allergen test particles into the chamber is effected by means of special particle distributors 28 (explained in more detail below with reference to FIGS. 8*a* and 8*b*), which are disposed at the two spaced-apart inlets 25 for allergen particles between which an air distribution pipe 27 is arranged (see FIG. 4). This particle distributor 28 and the constantly controlled slightly turbulent air flow inside the chamber guarantee homogeneous dispersion of the allergen in the air. Slow and continuous sedimentation of the allergen particles may be maintained. The rate of sedimentation for grass pollen allergen is about 1 m/min. Simultaneous measurements at three heights and at nine different points at every height of the chamber (using modified Burkhard pollen traps) show the high persistence of allergen dispersion (FIG. 5). The allergen load is constant within a long-term test over several hours within a standard deviation of only ≅5% (FIG. 6).

Figure 8A:
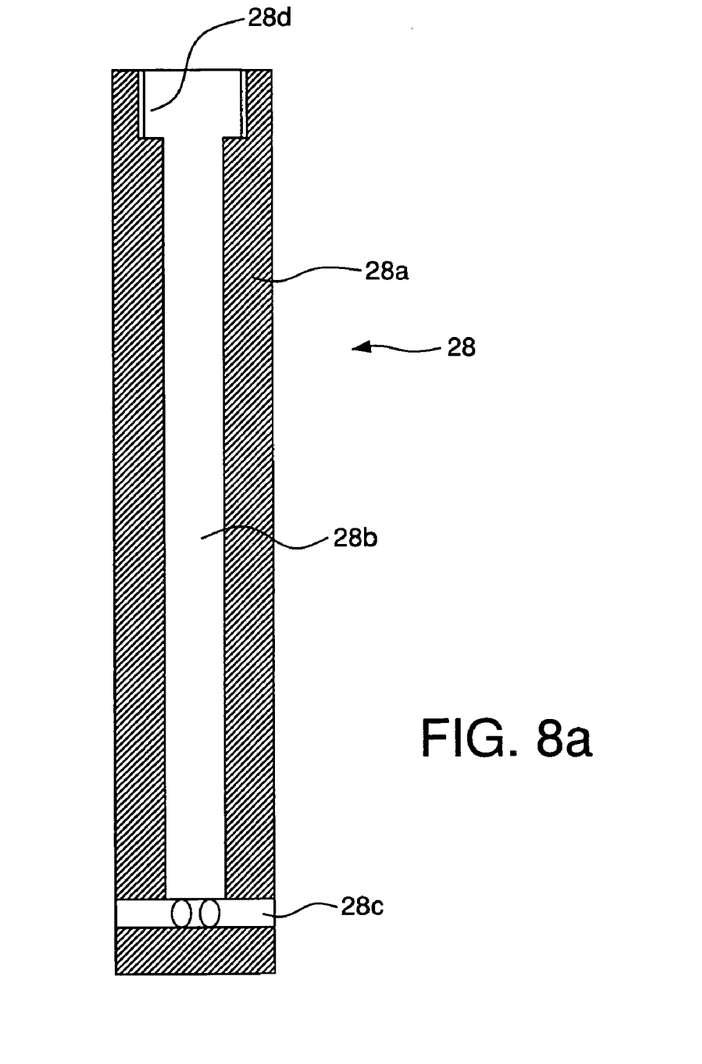
FIGS. 8a and 8b are longitudinal and transverse sections of a particle distributor according to the invention.
Figure 8B:
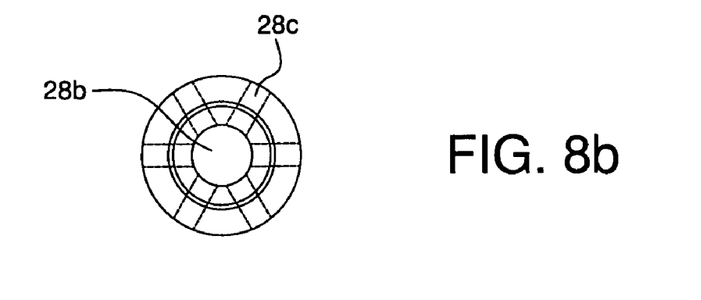

The particle distributor 28 according to FIGS. 8*a* and 8*b* has a cylindrical body 28*a* with an axial bore 28*b*, the upper end of which is enlarged and provided with an internal thread 28*d*, so as to screw it onto inlet 25. Radial bores 28*c* extend at the lower end of body 28*a* from the axial bore 28*b* towards the outside. Compressed air (typically 3 bar) blows allergens through the axial bore and then through the radial bores into the interior of the chamber, where they distribute in the air flow.

Sampling of Air

The allergen load of the air in the chamber is monitored in different ways during a test session: for routine procedures, a modified Burkhard object slide sampler is used for the continuous volumetric recording of the allergen particle count (i.e. pollen grains or house-dust mite faeces) per cubic meter of air at intervals of 5 minutes. At a flow rate of 8 cubic meters per minute (the flow rate recorded online by a thermo-anemometer FV A645-TH3 of Messrs. Alemo, Holzkirchen, Del.), the sampler is applied and the object slide coated with adhesive is exposed. The object slide is replaced every 5 minutes, and either analyzed automatically in a light-optical microscope (e.g. by Olympus, Hamburg, Del.) by means of digital image analysis, or the particles are counted by a biologist. In contrast to sampling techniques conventionally used, the flow of the trap is monitored automatically at short intervals of 5 seconds by means of a thermo-anemometer, and the reports are printed out as tables and graphs. This ensures a precise evaluation of the object slides and calculation of the allergen in the air.

In order to monitor the actual allergen content of the air (i.e. ng of major allergen supplied), a cyclone sampler is used for accumulating the allergen particles in the air for calculating the concentration of major allergen at a later time.

Immunochemical analysis is done by means of an ALK Indoor Allergen Analysis Kit® for ELISA technique according to the manufacturer's instructions. Finally the number of particles in the air may be measured continuously by way of laser nephelometry.

Validation of Allergen Load

In order to validate this concept, the VCC has to be compared to the conventional test by ocular challenge (OCT) and the widely-used test by nasal challenge (NCT), respectively, as well as the environmental challenge situation (ECS), as it can be found in field tests or park tests.

The allergen source used in OCT and NCT is a standardized allergen preparation, usually a dialyzate of pollen material or house-dust mite allergen. For the VCC native pollen grains or native house-dust mite faeces are used, both of them supplied by Allergon (Göteborg, Sweden). In case of ECS, native pollen grains and native house-dust mite faeces particles, respectively, are the allergen source as well. In case of OCT and NCT a dripper or nebulizer is used for applying the allergen. The exposure period is very short (only a few minutes, depending on the tearing, sneezing and blinking activities). In the VCC and the ECS native particles are dispensed in the air as aeroplankton. Both with the VCC and the ECS, the exposure period is several hours. There is no difference between VCC and ECS with respect to the allergen used, the application mode and the exposure period. There are, however, significant differences between OCT/NCT and ECS or VCC, respectively.

The aim of the VCC technology is to come as close as possible to the field situation. Therefore the allergen concentrations are chosen with respect to the field situation.

Studies with Pollen Allergens:

Studies with patients suffering from seasonal allergic conjunctivitis and/or seasonal allergic rhinitis require an allergen challenge by pollen. A grass pollen model and a birch pollen model are chosen for the VCC (the pollen grains used being Dactylis glomerata or Betula alba), as they are the most frequent allergen source in Austria. In field challenge studies, patients are exposed to a great variety of different pollen concentrations in the open. When correlating the pollen concentration in the air with the symptoms suffered by the patient, a threshold value of 250 pollen grains per cubic meter of air has to be assumed for an averagely sensitized patient. A dosis-dependent intensity of symptoms in the range of 500 to 2,500 grass pollen grains per cubic meter has been established, too. Comparing the various data of pollen concentration, it has to be taken into consideration that the "pollen warning services" obtain their data at a height of 15 meters and only refer to the daily average. The concentrations at ground level (1.5 meters) are much higher, however. This also applies to the peak values that are much higher than the daily average, which also includes the non-challenge during the night. The daily average has to be multiplied by 11 to 26 in order to compensate for the difference between data at a height of 1.5 meters and those obtained at 15 meters. Thus the concentration of 2,000 grass pollen per cubic meter corresponds to the average of 75 to 180 pollen per cubic meter, measured by means of a pollen trap at a height of 15 meters.

In field challenge studies patients are exposed to from several hundred to several thousand pollen grains per cubic meter of air. During the pollen season a concentration of about 2,000 pollen grains per cubic meter of air is very likely to be reached for several hours a day. Therefore the concentration normally used with the VCC is 2,000 pollen grains per cubic meter of air, stably throughout the challenging period and reproducible at every session. Higher concentrations increase the risk of bronchial attacks with allergic subjects. If the study protocol requires more moderate pollen challenge, a concentration of 1,500 grains or even less may be used in the VCC.

Proof of Consistency with OCT-ECS-VCC

In order to investigate the consistency of clinical results in various challenging modes, test subjects were tested at a grass pollen load of 2,000 grains per cubic meter in the VCC for 4 hours. At the end of the test session, an OCT was carried out using a grass pollen allergen solution (500 BU, ALK-Abello, Denmark). Two months later the test was repeated with the same subjects, the park model however being used as ECS instead of the VCC. Again a final OCT was carried out in order to prove consistency.

Figure 9:
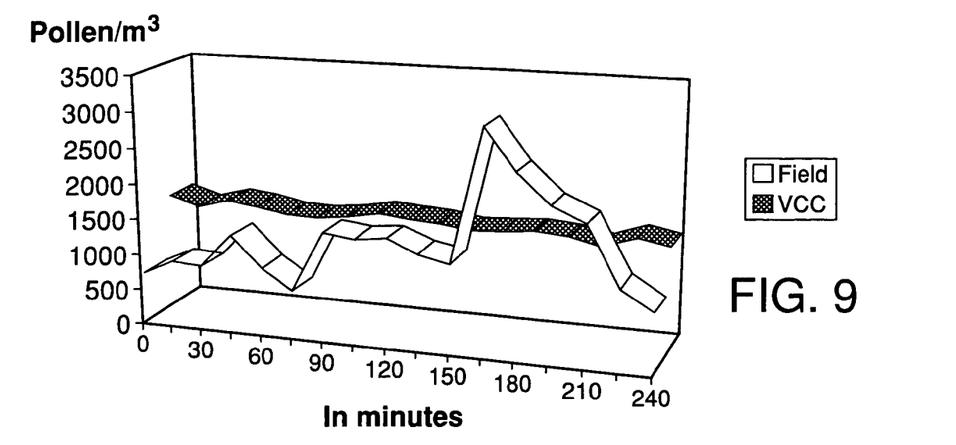
FIG. 9 is a graph of the variation of the grass pollen count in the course of 4 h in the field and in the test chamber according to the invention.
Figure 10:
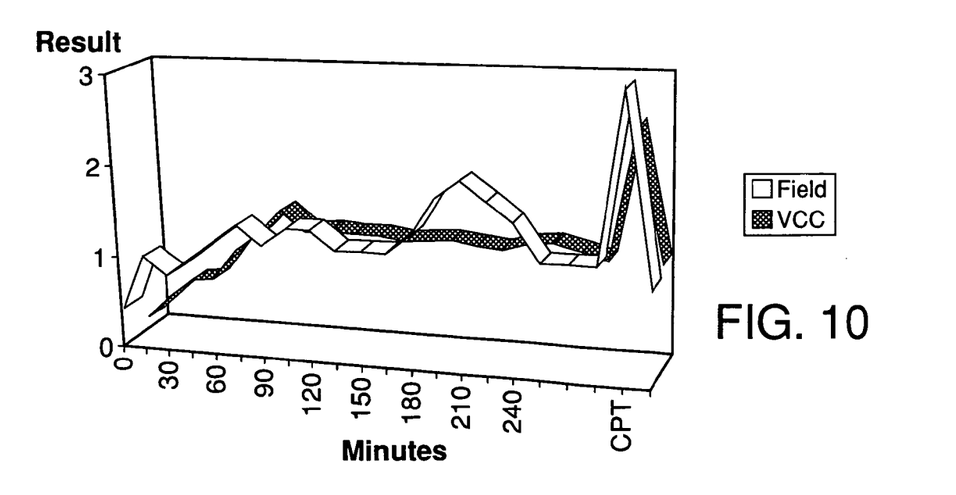
FIG. 10 is a graph of recordings of the subjective eye-itching of test subjects in the field and in the test chamber according to the invention.

The variations of pollen count in the VCC and the ECS are shown in FIG. 9. The concentrations are the same in both studies, but in the ECS, the variation is much more pronounced. Subjective symptoms recorded every 15 minutes are comparable in the ECS and the VCC as well as in both final OCTs (FIG. 10; subjective eye itching). The vascular reactions of the conjunctiva are monitored using conjuncitival digital imaging. Images were taken before the test session, after 4 hours of ECS and VCC, respectively, and after the OCT. There was a high consistency between the ECS and the VCC, and even between the OCT, the ECS and the VCC.

In order to establish the consistency of results, an OCT/NCT may be carried out in the VCC at the end of a test session. Apart from confirming the VCC session, doing so has an additional advantage: it is possible to increase the challenge with the OCT/NCT without risk at the end of a long-term challenge in order to verify if the drug used is still active. Increasing the pollen concentration to more than 2,000 grains per cubic meter in the VCC would bring about an increased risk of bronchial attacks.

Additional studies were carried out with patients by OCT/NCT as well as VCC and ECS. All the results were consistent, proving that the results of challenge tests in the VCC are generally comparable with field observations of the same number of patients in case of natural and seasonal exposure. As expected, because of the number of calculation tools, the VCC enables more precise and subtle results than field studies.

Studies with House-Mite Allergens:

Studies with patients suffering from permanent allergic conjunctivitis and/or permanent allergic rhinitis all through the year require an allergen test with house-dust mites so as to prove the specific sensitization to house-dust mite allergen. For the VCC, a model using the faeces of *Dermatophagoides pteronyssinus* is chosen, this being the most important source of house-dust mite allergy in Austria.

Usually the allergen content of a room is defined by samples of carpet and floor dust, but house-dust mite allergens also get into the air, and the concentration of allergens in the air is of fundamental interest for the sensitized patient. The relevant literature hardly gives any reports about the house-dust mite allergen concentration in the air. Sakaguchi et al., "Measurement of allergens associated with dust mite allergy", Int. Arch. Allergy Appl. Immunol. 1989, 90, pp. 190-193, have established concentrations of between 0.03 and 30 ng per cubic meter in various homes. The applicant has been able to establish that the threshold value for the averagely sensitized patient is 10 ng; starting at a concentration of 130 ng, an increased susceptibility to bronchial attacks has to be expected.

In case of natural exposure the average diameter of particles containing house-dust mite allergen is about 20 μm. These particles are not stable, however, they disintegrate to form several smaller particles having sizes of 5 μm or even less. Therefore it is not possible to calculate the allergen load by only counting the particles per square meter of air (as is possible with pollen allergens) without at the same time carrying out an immunochemical analysis as previously described.

Obtaining Clinical Results

During challenge in the chamber the patients are repeatedly examined at short intervals (usually 15 or 30 minutes). In order to obtain optimum data, not only the subjective symptoms are registered, but objective data are obtained as well. The subjective symptoms are input online in a database by patients themselves. Tests of lung function, nasal function, production of nasal secretion, etc. are carried out and evaluated by an assistant, who inputs the data into the database as well. Every single examination has to be carried out within one minute in order to ensure that every patient goes through a complete test run within 15 minutes.

CONCLUSIONS

Comparing the results of the conventional challenging tests, of field studies and of the VCC, a consistency of results is established, but without doubt the best reproducibility is achieved with the VCC. Comprehensive clinical studies have proven the quality of the VCC when testing numerous anti-allergenic compounds.

The invention claimed is:

1. An allergy test chamber comprising:
   a chamber capable of accommodating a person being tested for allergies;
   at least one first inlet for allergen-free air provided with an air flow distribution device distributing allergen-free air into said chamber,
   a first apparatus that in operation blows allergen-free air through said at least one first inlet and said air flow distribution device into said chamber,
   at least one second inlet for introducing allergen test particles into the chamber separately from the allergen-free air, said at least one second inlet being provided with a particle distributor that is disposed to distribute the allergen test particles into the interior of said chamber,
   a second apparatus that in operation blows allergen test particles through said at least one second inlet into said chamber,
   at least one outlet for air loaded with the distributed allergen test particles from said chamber, and
   a third apparatus that in operation sucks the air loaded with allergen test particles out of the interior of the chamber,
   the at least one first inlet and the at least one second inlet being spaced apart from the at least one outlet.

2. The allergy test chamber according to claim 1, wherein the at least one first inlet comprises an air supply pipe having a wall with a plurality of passage openings therein.

3. The allergy test chamber according to claim 1, wherein the air flow distribution device comprises air nozzles oriented in different directions.

4. The allergy test chamber according to claim 1, wherein the first and second inlets are spaced apart from each other.

5. The allergy test chamber according to claim 1, wherein the first and second inlets are arranged in at least one of the ceiling of the chamber and at least one sidewall of the chamber close to the ceiling, and the at least one outlet is provided in at least one of the floor of the chamber and at least one sidewall of the chamber close to the floor.

6. The allergy test chamber according to claim 1, wherein at least one multi-layer filter system aimed at reducing pollutants is inserted in the flow path of allergen-free air into the chamber.

7. The allergy test chamber according to claim 1, further comprising a device arranged to de-agglomerate the allergen particles before the allergen particles are introduced into the chamber.

8. The allergy test chamber according to claim 1, further comprising a device arranged to automatically dose allergen test particles and continuously or intermittently supply the allergen test particles into the chamber, the allergen test particles conveyed by a pressure or partial vacuum device.

9. The allergy test chamber according to claim 1, wherein a particle distributor is connected to the at least one second inlet.

10. The allergy test chamber according to claim 9, wherein the particle distributor comprises a body having an axial bore and radial bores extending from the axial bore to the outer periphery of the distributor.

11. The allergy test chamber according to claim 9, wherein the particle distributor comprises a baffle plate, the allergen test particles being conveyed through the second inlet by compressed air.

12. The allergy test chamber according to claim 9, wherein the particle distributor is mountable in such a way that the allergen test particles are introduced at those points where the flow interference of the allergen-laden air is zero.

13. The allergy test chamber according to claim 1, further comprising a climate module arranged to control climate parameters of the allergen-free air supplied into the chamber.

14. The allergy test chamber according to claim 13 wherein the climate module is equipped with a real-time control circuit arranged to control climate parameters.

15. The allergy test chamber according to claim 1, wherein the first inlet and the outlet are arranged to reduce the barometric pressure inside the chamber as compared to the barometric pressure outside the chamber.

16. The allergy test chamber according to claim 1, further comprising at least one measurement instrument arranged to identify representative parameters of the allergen test particles introduced into the chamber.

17. The allergy test chamber according to claim 16, further comprising at least one measurement instrument arranged to measure the particle concentration in the air inside the chamber.

18. The allergy test chamber according to claim 16, further comprising at least one measurement instrument each for every test subject in the chamber arranged to measure the individual allergen load.

19. The allergy test chamber according to claim 16, further comprising at least one particle collector arranged to accumulate the absolute particle quantity introduced in the course of one time unit for subsequently analyzing essential allergen parameters.

20. An allergy test chamber comprising:
a chamber capable of accommodating a person being tested for allergies;
at least one first inlet for allergen-free air provided with an air flow distribution device distributing allergen-free air into said chamber, a first apparatus that in operation blows allergen-free air through said at least one first inlet and said air flow distribution device to form a slightly turbulent air flow of allergen-free air in said chamber, at least one second inlet for introducing allergen test particles into the chamber separately from the allergen-free air, said at least one second inlet being provided with a particle distributor that is disposed to distribute the allergen test particles into the interior of said chamber and with the flow of the allergen-free air within said chamber, a second apparatus that in operation blows allergen test particles through said at least one second inlet into said slightly turbulent air flow of allergen-free air in said chamber, at least one outlet for air loaded with the distributed allergen test particles from said chamber, and a third apparatus that in operation sucks the air loaded with allergen test particles out of the interior of the chamber, the at least one first inlet and the at least one second inlet being spaced apart from the at least one outlet.

21. An allergy test chamber comprising:

a chamber capable of accommodating a person being tested for allergies;

at least one first inlet for allergen-free air arranged in at least one of the ceiling of the chamber and at least one sidewall of the chamber close to the ceiling and provided with an air flow distribution device distributing allergen-free air into said chamber with a turbulent air flow, a first apparatus that in operation blows allergen-free air through said at least one first inlet and said air flow distribution device into said chamber, at least one second inlet arranged in at least one of the ceiling of the chamber and at least one sidewall of the chamber close to the ceiling and spaced apart from said first inlet for introducing allergen test particles into the chamber separately from the allergen-free air, said at least one second inlet being provided with a particle distributor that is disposed to distribute the allergen test particles into the interior of said chamber and with the flow of the allergen-free air within said chamber, a second apparatus that in operation blows allergen test particles through said at least one second inlet into said turbulent air flow in said chamber, at least one outlet provided in at least one of the floor of the chamber and at least one sidewall of the chamber close to the floor for air loaded with the distributed allergen test particles from said chamber, and a third apparatus that in operation sucks the air loaded with allergen test particles out of the interior of the chamber.

22. An allergy test chamber according to claim 21, wherein said particle distributor is arranged to distribute the allergen particles horizontally before the allergen particles become mixed with the flow of allergen-free air.

* * * * *